United States Patent
Kneller

(10) Patent No.: US 7,939,517 B2
(45) Date of Patent: May 10, 2011

(54) 1,4,6-ANDROSTATRIENE-3,17-DIONE ("ATD") FOR THERAPEUTIC USES

(76) Inventor: Bruce W. Kneller, Randolph, MA (US)

( * ) Notice: Subject to any disclaimer, the term of this patent is extended or adjusted under 35 U.S.C. 154(b) by 863 days.

(21) Appl. No.: 11/187,043

(22) Filed: Jul. 22, 2005

(65) Prior Publication Data

US 2006/0154909 A1    Jul. 13, 2006

Related U.S. Application Data

(60) Provisional application No. 60/590,108, filed on Jul. 21, 2004.

(51) Int. Cl.
  *A61K 31/56* (2006.01)
  *A61K 31/5685* (2006.01)
(52) U.S. Cl. .................. 514/177; 514/170
(58) Field of Classification Search .......... 514/170, 514/177
  See application file for complete search history.

(56) References Cited

U.S. PATENT DOCUMENTS

| | | | | |
|---|---|---|---|---|
| 2,877,239 A | * | 3/1959 | Agnello et al. | 514/178 |
| 2,882,282 A | * | 4/1959 | Agnello et al. | 540/83 |
| 2,883,379 A | * | 4/1959 | Moreland et al. | 540/83 |
| 4,596,797 A | * | 6/1986 | Schweikert et al. | 514/177 |
| 5,162,337 A | * | 11/1992 | Elbrecht et al. | 514/300 |

OTHER PUBLICATIONS

Parish et al. Design and Synthesis of new Steroidal Inhibitors of Estrogen Synthase (aromatase) Lipids, 35:3, p. 271-277.*
Brodie, Overview of Recent Development of Aromatase Inhibitors, Cancer Research 42, 3312s-3314s.*
Shearer, HIV/AIDS: Waiting for a cure, Journal of Allergy and Clinical Immunology, 2008, pp. 1-2.*
Merriam-Webster's Collegiate Dictionary, 1996, Tenth Edition, 3 Page.*
Parish et al. Design and Synthesis of new Steroidal Inhibitors of Estrogen Synthase (aromatase) Lipids, 35:3, p. 271-277.*
Brodie, Overview of Recent Development of Aromatase Inhibitors, Cancer Research 42, 3312s-3314s.*
Shearer, HIV/AIDS: Waiting for a cure, Journal of Allergy and Clinical Immunology, 2008, pp. 1-2.*
Schwarzel et al., Studies on the Mechanism of Estrogen Biosynthesis. VIII. The Development of Inhibitors in Human Placenta, Endocrinology, 92:3, 197.*
Marsh et al., Aromatase Inhibitors, Synthesis and Biological activity of Androstenedione, Journal Medicinal Chemistry, 28:6 788-795, 1985.*
Schwarzel et al., Studies on the Mechanism of Estrogen Biosynthesis. VIII. The Development of Inhibitors in Human Placenta, Endocrinology, 92:3, 1973.*
Smith et al., Aormatase Inhibitors in Breast Cancer, The New England Journal of Medicine, 348;24, pp. 2431-2442, 2003.*

* cited by examiner

*Primary Examiner* — Johann R Richter
*Assistant Examiner* — Andriae M Holt
(74) *Attorney, Agent, or Firm* — Morse, Barnes-Brown & Pendleton, P.C.; Lisa M. Treannie, Esq.

(57) ABSTRACT

A composition having at least one modified or derivative of 1,4,6-androstatriene-3,17-dione ("ATD") will improve the health of mammalian subjects. The improvement of health is achieved with the administration of an effective amount of at least one modified or derivative of 1,4,6-androstatriene-3,17-dione. Particularly, health is improved for a subject suffering with a gynecomastia and/or estrogen-dependent cancer. Also, subjects recovering from steroid misuse/abuse will benefit from treatment in accordance with the present invention.

8 Claims, No Drawings

1,4,6-ANDROSTATRIENE-3,17-DIONE ("ATD") FOR THERAPEUTIC USES

This application claims the benefit of U.S. Provisional Application No. 60/590,108, filed Jul. 21, 2004, which is incorporated herein by reference.

BACKGROUND OF THE INVENTION

1. Technical Field

The present invention relates to a non-androgenic steroidal chemical. More particularly, the invention relates to the chemical 1,4,6-androstatriene-3,17-dione ("ATD") and its metabolites and analogs for therapeutic use in humans and animals as an anti-aromatase, testosteronegenic and anti-estrogenic compound.

2. Description of Related Art

Estrogens are vital to human growth, development, sexual differentiation and other functions. However, excess estrogen may lead to diseases or problems in women including: weight gain, fibrocystic breast disease, migraine headaches, menstrual disturbances, endometriosis and certain types of PMS. Men may experience infertility and gynecomastia with excess levels of estrogen.

The enzyme aromatase is required for the conversion of androgens into estrogens. Because of its action, aromatase has been the target of pharmaceutical therapies aimed at decreasing circulating levels of estrogen. Inhibitors of aromatase generally act by blocking the aromatization of endogenous androgens, such as testosterone, into estrogens. The effect is a decrease in levels of circulating estrogens and a concomitant increase in levels of circulating androgens. Modern cancer treatments may utilize aromatase inhibitors to combat tumors that depend on estrogen for growth. For instance, the growth of many breast cancers is promoted by estrogens. Most estrogen after menopause comes from areas outside of the ovaries by the action of aromatase, when the ovaries are no longer producing estrogen. Aromatase inhibitors may therefore be used to treat estrogen-dependent tumors after menopause. Aromatase inhibitors simply prevent or severely limit aromatizable androgens from being converted to estrogen. Moreover, aromatase inhibition may be an element in a myriad of other therapies including increasing endogenous androgen levels without a concomitant rise or even change in estrogen levels. What is needed is an improved inhibitor of the aromatase enzyme.

While aromatase inhibitors have been effectively used to decrease circulating levels of estrogen, currently available treatments have substantial room for improvement. Aromatase inhibitors include 4-hydroxyandrostenedione and FORMESTANE which are inherent anabolic compounds. Because of their compositions, they often have undesirable anabolic and androgenic effects. In contrast, 3-beta-hydroxyandrost-4-ene-6,17-dione ("3-OHAT") and androst-4-ene-3,6,17-trione (AT) are non-androgenic compounds. But they may require frequent and high dosing because of their relatively low potency and rapid metabolization. Many aromatase inhibitors will cause a rise in endogenous androgen levels but also cause a precipitous and possibly unwanted decrease in endogenous estrogen levels when used in men. Because currently available aromatase inhibitors may have undesirable side-effects or lack adequate potency or are very expensive to manufacture currently or decrease endogenous estrogen levels too much in men, improved anti-aromatase compounds are needed.

SUMMARY OF THE INVENTION

A composition having modified or derivative of 1,4,6-androstatriene-3,17-dione ("ATD") will improve the health of mammalian subjects. The improvement in health is achieved with the administration of an effective amount of the at least one modified or derivative of 1,4,6-androstatriene-3,17-dione. Particularly, health is improved with administration of an effective amount for a mammal suffering from a gynecomastia, and/or estrogen-dependent cancer. Also, mammals recovering from steroid misuse/abuse will benefit from treatment in accordance with the present invention. Other improvements found to occur with an administration of ATD is that growth is enhanced and/or stimulated in developing mammals, particularly for short children whose epiphesial plates have not closed yet, by delaying the closure of the plates. Male fertility can be improved via one or more effects on either gonadotropin releasing hormone, LH or FSH with administration of ATD. Administration of an effective amount of ATD increases athletic performance by increasing testosterone and lean muscle mass, shortens the recovery period in cases of severe trauma or burns, and improves a mood of a mammal through improved anabolism.

DETAILED DESCRIPTION

The aromatase enzyme catalyzes the aromatization of endogenous androgens into estrogens. Inhibiting the enzyme's activity usually leads to a decrease in levels of circulating estrogens and an increase in levels of circulation androgens. Chemicals which inhibit the aromatase enzyme present many potential therapeutic applications.

According to the present invention, 1,4,6-androstatriene-3,17-dione ("ATD") is a more effective anti-aromatase compound than those currently available, and additionally, at specific dosing, ATD is capable of greatly increasing testosterone levels without a concomitant decrease of estrogen levels in men.

ATD acts as a suicide substrate by irreversibly binding to the aromatase enzyme and shutting down its activity. Because it is a non-androgenic compound, ATD has fewer side effects associated with anabolic/androgenic steroid use. Recent studies have demonstrated that ATD is more potent than 3-OHAT or AT. Specifically, ATD has a Ki of 0.18 micromolar ($\mu$M) and AT has a Ki of 0.43 $\mu$M. A lower Ki value means the inhibitor binds more tightly to the enzyme and yields greater potency. The ratio of the Ki values indicates that AT must be used in a concentration 2.39 times greater than that of ATD to achieve the same effect. In other words, ATD is close to three times more potent than AT, requiring only 30-40% of the dose of AT to elicit the same effect. Because it is administered in smaller doses, costs of use of ATD may also be lower. The savings may be passed on to the consumer and/or provide greater profits to the manufacturer. Additionally, with oral or percutaneous/transdermal doses of 25 mg to 150 mg per day in men, ATD will cause a significant increase in endogenous androgen levels with little or no decrease in endogenous estrogen.

Because the invention is more potent than traditionally used anti-aromatases, the invention may be more effective therapeutically. The invention has many potential uses, including cancer treatment, gynecomastia treatment, treatment of growth and development issues, and treatment of abuse or misuse of anabolic steroids.

Cancer Treatment

Many breast cancers have estrogen receptors and their growth can be stimulated by estrogen. ATD may provide a more effective means of aromatase inhibition to fight such cancers.

Gynecomastia Treatment

Gynecomastia is the growth of breast tissue in men. In minor cases, it may be just a cosmetic nuisance. But occasionally, gynecomastia can lead to breast cancer in men. ATD may provide more effective treatment than those currently available.

Growth and Development

Estrogens have an essential role in the regulation of bone maturation and importantly in the closure of growth plates in both sexes. The invention could be used in children of short stature to increase terminal linear height.

Treatment After Abuse/Misuse of Anabolic Steroids

Competitive athletes and body builders may use anabolic steroids to increase their performance and physical appearance. The synthetic/exogenous steroids replace natural testosterone. Among the short term effects are increased strength and muscle mass but prolonged use may lead to many harmful effects including liver damage, sterility and psychiatric side effects. As a consequence of feed-back inhibition, the body's endogenous production of androgens may be shut down. The invention may assist the recovery of such individuals by increasing plasma androgen levels as the body recovers its ability to produce adequate amounts of the hormone endogenously.

Other uses of ATD include improving male fertility via effects on gonadotropin releasing hormone, luteinizing hormone ("LH") and follicle-stimulating hormone ("FSH"), increasing lateral height in short children whose epiphysial plates have not closed yet by delaying the closure of such, increasing athletic performance through increasing testosterone and lean muscle mass, speeding up recovery in cases of severe trauma or burns, and improving mood through improved anabolism. ATD may also be utilized for hormone/androgen replacement therapy in men without causing a concomitant drop in endogenous estrogen levels when utilized orally or by percutaneous/transdermal administration in doses of 25 mg to 150 mg per day.

For purposes of this application, any method that comprises a numerical (ie. first, second, third, etc.) administering of a numerical (ie. first, second, third, etc.) effective amount of at least one modified or derivative of 1,4,6-androstatriene-3,17-dione ("ATD") to said mammal, the numerical amount is intended for distinguishing purposes only and not for use as order or quantity in and of itself.

Desired forms of the present invention include, but are not limited to at least one modified or derivative of 1,4,6-androstatriene-3,17-dione ("ATD"), such as:

1,4,6-androstatriene-3-one-17-ol;
1,4,6-androstatriene-3-ol, 17-ol;
1,4,6-androstatriene-3-ol-17-one;
1,4,6-androstatriene-3-ol, 17-ol;
1,4,6-androstatriene-3-one-17-azine;
1,4,6-androstatriene-17-one, 3-azine;
1,4,6-androstatriene-3-ol-17-azine;
1,4,6-androstatriene-17-ol-3-azine; and
a c-3 modified, c-17 modified or c-3 & c-17 modified compound of the group further comprising:
1,4,6-androstatriene-3-one-17-ol;
1,4,6-androstatriene-3-ol, 17-ol;
1,4,6-androstatriene-3-ol-17-one;
1,4,6-androstatriene-3-one-17-azine;
1,4,6-androstatriene-17-one, 3-azine;
1,4,6-androstatriene-3-ol-17-azine;
1,4,6-androstatriene-17-ol-3-azine.

Further, the analogs and metabolites of 1,4,6-androstatriene-3,17-dione ("ATD") include but are not limited to:

1,4,6-androstatriene-3,17-dione;
1,4,6-androstatriene;
1,4,6-androstatriene-3-one;
1,4,6-androstatriene-17-one;
1,4,6-androstatriene-3-ol;
1,4,6-androstatriene-17-ol;
1,4,6-androstatriene-3,17-diol;
1,4,6-androstatriene-3-ol-17-one;
1,4,6-androstatriene-17-ol-3-one;
17a-methyl-1,4,6-androstatriene;
17a-methoxy-1,4,6-androstatriene;
17a-hydroxymethylene-1,4,6-androstatriene;
1,4,6-androstatriene-4-ol;
1,4,6-androstatriene-3-one-4-ol;
1,4,6-androstatriene-17-one-4-ol;
1,4,6-androstatriene-3,17-dione-4-ol;
1,4,6-androstatriene-3,4-diol;
1,4,6-androstatriene-4,17-ol;
1,4,6-androstatriene-3,4,17-triol;
1,4,6-androstatriene-3,4-diol-17-one;
17a-methyl-1,4,6-androstatriene-3,4-diol;
17a-methyl-1,4,6-androstatriene-4,17b-ol;
17a-methyl-1,4,6-androstatriene-3,4,17b-triol;
17a-methyl-1,4,6-androstatriene-3,17a-diol-3-one;
17a-methoxy-1,4,6-androstatriene-3,4-diol;
17a-methoxy-1,4,6-androstatriene-4,17b-ol;
17a-methoxy 1,4,6-androstatriene-3,4,17b-triol;
17a-methoxy-1,4,6-androstatriene-3,17a-diol-3-one;
17a-hydroxymethylene-1,4,6-androstatriene-3,4-diol;
17a-hydroxymethylene-1,4,6-androstatriene-4,17b-ol;
17a-hydroxymethylene-1,4,6-androstatriene-3,4,17b-triol;
17a-hydroxymethylene-1,4,6-androstatriene-3,17a-diol-3-one;
1,4,6-androstatriene-3-azine;
1,4,6-androstatriene-3-azo-17b-ol;
1,4,6-androstatriene-3-azo-17-one;
1,4,6-androstatriene-3-azo-4,17b-ol;
17a-methyl-1,4,6-androstatriene-3-azine;
17a-methyl-1,4,6-androstatriene-3-azo-17b-ol;
17a-methyl-1,4,6-androstatriene-3-azo-17-one;
17a-methyl-1,4,6-androstatriene-3-azo-4,17b-ol;
17a-methoxy-1,4,6-androstatriene-3-azine;
17a-methoxy-1,4,6-androstatriene-3-azo-17b-ol;
17a-methoxy-1,4,6-androstatriene-3-azo-17-one;
17a-methoxy-1,4,6-androstatriene-3-azo-4,17b-ol;
17a-hydroxymethylene-1,4,6-androstatriene-3-azine;
17a-hydroxymethylene-1,4,6-androstatriene-3-azo-17b-ol;
17a-hydroxymethylene-1,4,6-androstatriene-3-azo-17-one;
17a-hydroxymethylene-1,4,6-androstatriene-3-azo-4,17b-ol;
1,4,6-androstatriene-4-acetate;
1,4,6-androstatriene-3-one-4-acetate;
1,4,6-androstatriene-17-one-4-acetate;
1,4,6-androstatriene-3,17-dione-4-acetate;
1,4,6-androstatriene-3-ol-4-acetate;
1,4,6-androstatriene-17b-ol-4-acetate;
1,4,6-androstatriene-3,17-diol-acetate;
1,4,6-androstatriene-3-ol-17-one-4-acetate;
17a-methyl-1,4,6-androstatriene-4-acetate;
17a-methyl-1,4,6-androstatriene-3-one-4-acetate;
17a-methyl-1,4,6-androstatriene-3-ol-4-acetate;

17a-methyl-1,4,6-androstatriene-17b-ol-4-acetate;
17a-methyl-1,4,6-androstatriene-3,17b-diol-acetate;
17a-methoxy-1,4,6-androstatriene-4-acetate;
17a-methoxy-1,4,6-androstatriene-3-one-4-acetate;
17a-methoxy-1,4,6-androstatriene-3-ol-4-acetate;
17a-methoxy-1,4,6-androstatriene-17b-ol-4-acetate;
17a-methoxy-1,4,6-androstatriene-3,17b-diol-acetate;
17a-hydroxymethylene-1,4,6-androstatriene-4-acetate;
17a-hydroxymethylene-1,4,6-androstatriene-3-one-4-acetate;
17a-hydroxymethylene-1,4,6-androstatriene-3-ol-4-acetate;
17a-hydroxymethylene-1,4,6-androstatriene-17b-ol-4-acetate;
17a-hydroxymethylene-1,4,6-androstatriene-3,17b-diol-acetate;
1,4,6-estratriene-3,17-dione;
1,4,6-estratriene;
1,4,6-estratriene-3-one;
1,4,6-estratriene-17-one;
1,4,6-estratriene-3-ol;
1,4,6-estratriene-17-ol;
1,4,6-estratriene-3,17-diol;
1,4,6-estratriene-3-ol-17-one;
1,4,6-estratriene-17-ol-3-one;
17a-methyl-1,4,6-estratriene;
17a-methoxy-1,4,6-estratriene;
17a-hydroxymethylene-1,4,6-estratriene;
1,4,6-estratriene-4-ol;
1,4,6-estratriene-3-one-4-ol;
1,4,6-estratriene-17-one-4-ol;
1,4,6-estratriene-3,17dione-4-ol;
1,4,6-estratriene-3,4-diol;
1,4,6-estratriene-4,17-ol;
1,4,6-estratriene-3,4,17-triol;
1,4,6-estratriene-3,4-diol-17-one;
17a-methyl-1,4,6-estratriene-3,4-diol;
17a-methyl-1,4,6-estratriene-4,17b-ol;
17a-methyl 1,4,6-estratriene-3,4,17b-triol;
17a-methyl-1,4,6-estratriene-3,17a-diol-3-one;
17a-methoxy-1,4,6-estratriene-3,4-diol;
17a-methoxy-1,4,6-estratriene-4,17b-ol;
17a-methoxy1,4,6-estratriene-3,4,17b-triol;
17a-methoxy-1,4,6-estratriene-3,17a-diol-3-one;
17a-hydroxymethylene-1,4,6-estratriene-3,4-diol;
17a-hydroxymethylene-1,4,6-estratriene-4,17b-ol;
17a-hydroxymethylene-1,4,6-estratriene-3,4,17b-triol;
17a-hydroxymethylene-1,4,6-estratriene-3,17a-diol-3-one;
1,4,6-estratriene-3-azine;
1,4,6-estratriene-3-azo-17b-ol;
1,4,6-estratriene-3-azo-17-one;
1,4,6-estratriene-3-azo-4,17b-ol;
17a-methyl-1,4,6-estratriene-3-azine;
17a-methyl-1,4,6-estratriene-3-azo-17b-ol;
17a-methyl-1,4,6-estratriene-3-azo-17-one;
17a-methyl-1,4,6-estratriene-3-azo-4,17b-ol;
17a-methoxy-1,4,6-estratriene-3-azine;
17a-methoxy-1,4,6-estratriene-3-azo-17b-ol;
17a-methoxy-1,4,6-estratriene-3-azo-17-one;
17a-methoxy-1,4,6-estratriene-3-azo-4,17b-ol;
17a-hydroxymethylene-1,4,6-estratriene-3-azine;
17a-hydroxymethylene-1,4,6-estratriene-3-azo-17b-ol;
17a-hydroxymethylene-1,4,6-estratriene-3-azo-17-one;
17a-hydroxymethylene-1,4,6-estratriene-3-azo-4,17b-ol;
1,4,6-estratriene-4-acetate;
1,4,6-estratriene-3-one-4-acetate;
1,4,6-estratriene-17-one-4-acetate;
1,4,6-estratriene-3,17-dione-4-acetate;
1,4,6-estratriene-3-ol-4-acetate;
1,4,6-estratriene-17b-ol-4-acetate;
1,4,6-estratriene-3,17-diol-acetate;
1,4,6-estratriene-3-ol-17-one-4-acetate;
17a-methyl-1,4,6-estratriene-4-acetate;
17a-methyl-1,4,6-estratriene-3-one-4-acetate;
17a-methyl-1,4,6-estratriene-3-ol-4-acetate;
17a-methyl-1,4,6-estratriene-17b-ol-4-acetate;
17a-methyl-1,4,6-estratriene-3,17b-diol-acetate;
17a-methoxy-1,4,6-estratriene-4-acetate;
17a-methoxy-1,4,6-estratriene-3-one-4-acetate;
17a-methoxy-1,4,6-estratriene-3-ol-4-acetate;
17a-methoxy-1,4,6-estratriene-17b-ol-4-acetate;
17a-methoxy-1,4,6-estratriene-3,17b-diol-acetate;
17a-hydroxymethylene-1,4,6-estratriene-4-acetate;
17a-hydroxymethylene-1,4,6-estratriene-3-one-4-acetate;
17a-hydroxymethylene-1,4,6-estratriene-3-ol-4-acetate;
17a-hydroxymethylene-1,4,6-estratriene-17b-ol-4-acetate; and
17a-hydroxymethylene-1,4,6-estratriene-3,17b-diol-acetate.

While the invention has been particularly shown and described with reference to a preferred embodiment, it will be understood by those skilled in the art that various changes in form and detail may be made therein without departing from the spirit and scope of the invention.

What is claimed is:

1. A method for treating a human male to increase athletic performance by increasing testosterone without causing concomitant reduction in endogenous estrogen levels comprising: orally administering to a human male to be treated an effective amount of at least one compound selected from the group consisting of: 1,4,6-androstatriene-3,17-dione; 1,4,6-androstatriene-3-one-17-ol; 1,4,6-androstatriene-3,17-diol; 1,4,6-androstatriene-3-ol-17-one; 1,4,6-androstatriene-3-one-17-azine; 1,4,6-androstatriene-17-one,3-azine; 1,4,6-androstatriene-3-ol-17-azine; and 1,4,6-androstatriene-17-ol-3-azine.

2. A method for treating a human male to increase athletic performance by increasing testosterone without causing concomitant reduction in endogenous estrogen levels comprising: orally administering to a human male to be treated an effective amount of at least one compound selected from the group consisting of: 1,4,6-androstatriene-3,17-dione; 1,4,6-androstatriene-3-one-17-ol; 1,4,6-androstatriene-3,17-diol; 1,4,6-androstatriene-3-ol-17-one; 1,4,6-androstatriene-3-ol-17-azine; 1,4,6-androstatriene-3-one-17-azine; 1,4,6-androstatriene-17-one,3-azine; and 1,4,6-androstatriene-17-ol-3-azine, wherein said compound is further modified at c-3, c-17, or c-3 and c-17.

3. The method of claim 2 wherein the further modification at c-3 is selected from the group consisting of ester, diester, ether, and diether and wherein the further modification at c-17 is independently selected from the group consisting of ester, diester, ether, and diether.

4. The method according to claim 3 wherein the ester is selected from the group consisting of: formate; acetate; propionate; butyrate; valerate; hexanoate; heptanoate; octanoate; nonanoate; decanoate; undecanoate; undecylenate; cyclohexylmethylcarbonate; methyl carbonate; ethyl carbonate; propyl carbonate; carbonate; benzoate; phenylpropionate; hemisuccinate; dichloroacetate; hexahydrobenzoate; isobutyrate; caproate; isocaproate; 4-methylvalerate; tosylate; laurate; methyl ester; ethyl ester; and buciclate.

5. The method according to claim 3 wherein the ether is selected from the group consisting of: tetrahydropyranyl ether; methyl ether; cyclopenten-1-yloxy ether; cyclopentyl ether; cyclohexyl ether; methoxycyclopentyl ether; and ethyl ether.

6. The method of claim 1 or claim 2 wherein said at least one compound is administered via cyclodextran, liposomal or PEG solution.

7. The method of claim 2 wherein the at least one compound is selected from the group consisting of: 1,4,6-androstatriene-3-azo-17b-ol; 1,4,6-androstatriene-3-azo-17-one; 17a-methoxy-1,4,6-androstatriene-3-azo-17b-ol; 1,4,6-estratriene-3,17-dione; 1,4,6-estratriene-3,17-diol; 1,4,6-estratriene-3-ol-17-one; 1,4,6-estratriene-17-ol-3-one; 1,4,6-estratriene-3,17-dione-4-ol; 1,4,6-estratriene-3-azo-17b-ol; 1,4,6-estratriene-3-azo-17-one; 17a-methoxy-1,4,6-estratriene-3-azo-17b-ol; 17a-methoxy-1,4,6-estratriene-3-azo-17-one; and 17a-methoxy-1,4,6-estratriene-3,17b-diol-acetate.

8. The method of claim 1, claim 2 or claim 7 wherein said administering comprises administering said at least one compound to a male at a dose of from about 25 mg to about 150 mg per day.

* * * * *